(12) United States Patent
Eguchi et al.

(10) Patent No.: US 12,343,126 B2
(45) Date of Patent: Jul. 1, 2025

(54) BIOLOGICAL INFORMATION ACQUISITION DEVICE

(71) Applicant: SEIKO EPSON CORPORATION, Tokyo (JP)

(72) Inventors: Tsukasa Eguchi, Matsumoto (JP); Hitoshi Tsuchiya, Shiojiri (JP); Ayae Sawado, Kai (JP); Akira Ikeda, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 272 days.

(21) Appl. No.: 17/655,363

(22) Filed: Mar. 17, 2022

(65) Prior Publication Data
US 2022/0296109 A1  Sep. 22, 2022

(30) Foreign Application Priority Data
Mar. 19, 2021  (JP) .................................. 2021-045650

(51) Int. Cl.
*A61B 5/026* (2006.01)
*A61B 5/024* (2006.01)

(52) U.S. Cl.
CPC ........ *A61B 5/0261* (2013.01); *A61B 5/02427* (2013.01)

(58) Field of Classification Search
CPC ........................ A61B 5/0261; A61B 5/02427
See application file for complete search history.

(56) References Cited

U.S. PATENT DOCUMENTS

| 6,608,668 B2 * | 8/2003 | Gharib ................. A61B 5/0261 356/28 |
| 2006/0094941 A1 * | 5/2006 | Cho ........................ A61B 5/01 600/549 |
| 2017/0179682 A1 * | 6/2017 | Ishii ..................... A61B 5/1455 |
| 2020/0323438 A1 * | 10/2020 | Sawada et al. ........... G01F 1/66 |

FOREIGN PATENT DOCUMENTS

| JP | 2017046802 A | 3/2017 |
| JP | 2018038546 A | 3/2018 |
| JP | 2020072823 A | 5/2020 |
| WO | 2014136242 A1 | 9/2014 |

OTHER PUBLICATIONS

Office Action for JP Patent Application No. JP2021045650, issued on Aug. 20, 2024, 8 pages of Office Action.

* cited by examiner

*Primary Examiner* — Bo Joseph Peng
(74) *Attorney, Agent, or Firm* — CHIP LAW GROUP

(57) ABSTRACT

A biological information acquisition device includes a light source configured to emit a laser beam; a light branching element configured to branch the laser beam into a first luminous flux and a second luminous flux; a first light receiving element configured to receive the first luminous flux; a second light receiving element configured to receive scattered light generated by scattering of the second luminous flux incident on an inspection site of a living body; a differential circuit to which the first light receiving element and the second light receiving element are coupled; a signal processing unit configured to obtain biological fluid information by processing a light detection signal output via the differential circuit; and a first light shielding part configured to reduce the scattered light incident on the first light receiving element.

9 Claims, 6 Drawing Sheets

BIOLOGICAL INFORMATION ACQUISITION DEVICE

The present application is based on, and claims priority from JP Application Serial Number 2021-045650, filed Mar. 19, 2021, the disclosure of which is hereby incorporated by reference herein in its entirety.

BACKGROUND

1. Technical Field

The present disclosure relates to a biological information acquisition device that acquires biological fluid information such as a blood flow, a blood volume, a blood flow rate, a pulse, and the like in living tissue using scattered light from biological tissue.

2. Related Art

JP-A-2020-72823 is mentioned as a document related to this type of biological fluid information acquisition device and biological information acquisition device JP-A-2020-72823 describes a device that includes a sensor part in which a semiconductor laser and a light receiving element are disposed on the same plane, and is configured to acquire biological fluid information in biological tissue using scattered light from the biological tissue.

In JP-A-2020-72823, in order to enhance a signal-to-noise ratio (SN ratio) of a light detection signal, a fully differential circuit is configured using a light receiving element in which internally reflected light is dominant and a light receiving element in which bio-scattered light is dominant.

However, because scattered light from a living body is light having an optical spread, there is a problem in that it is difficult to obtain a high SN ratio because the scattered light is mixed even on the side of the light receiving element in which internally reflected light is dominant.

SUMMARY

In order to solve the above-described problems, a biological fluid information acquisition device and biological information acquisition device according to the present disclosure includes: a light source configured to emit a laser beam; a light branching element configured to branch the laser beam into a first luminous flux and a second luminous flux; a first light receiving element configured to receive the first luminous flux; a second light receiving element configured to receive scattered light generated by scattering of the second luminous flux incident on an inspection site of a living body; a differential circuit to which the first light receiving element and the second light receiving element are coupled; a signal processing unit configured to obtain biological fluid information by processing a light detection signal output via the differential circuit; and a first light shielding part configured to reduce the scattered light incident on the first light receiving element.

DESCRIPTION OF EXEMPLARY EMBODIMENTS

Figure 1:
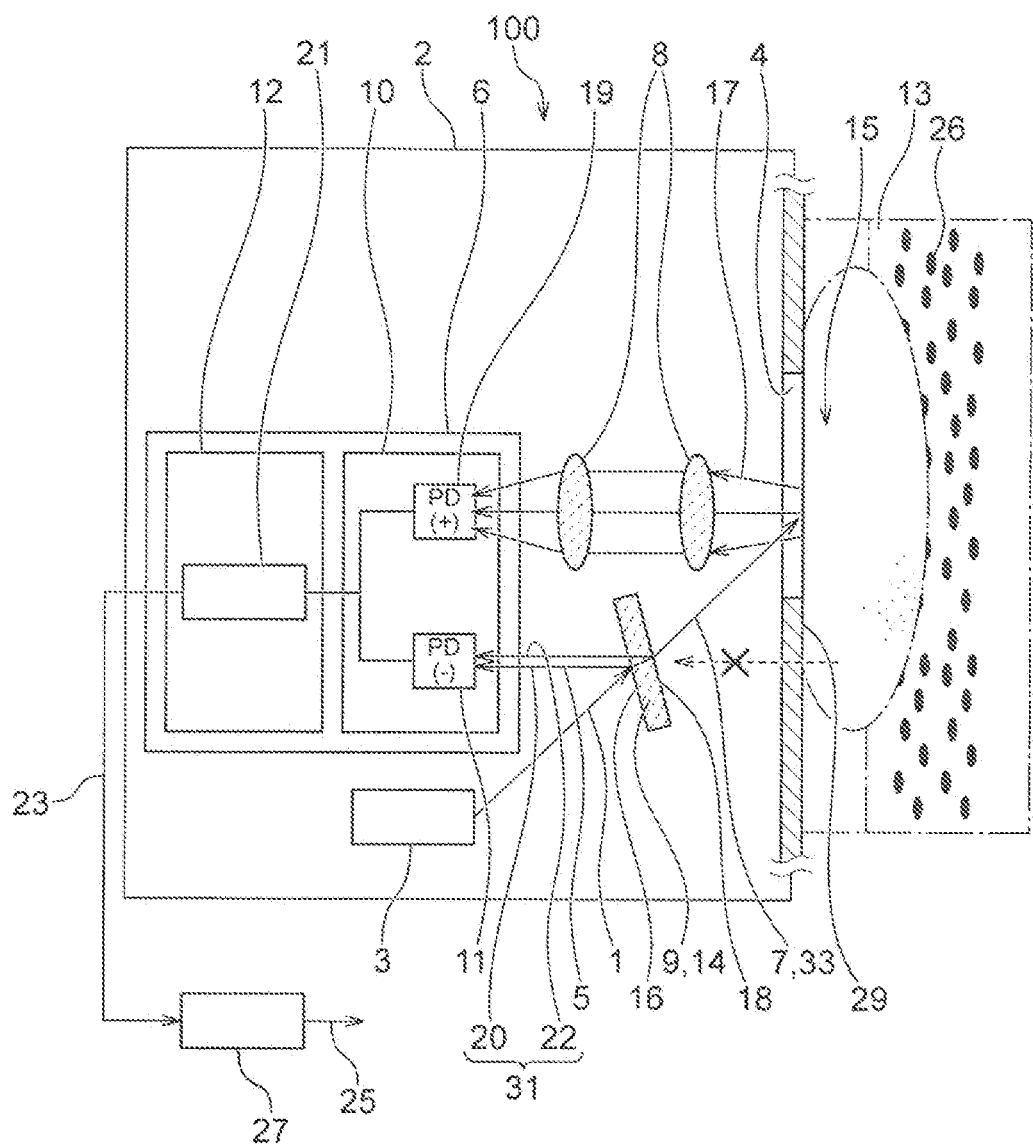
FIG. 1 is an overall schematic configuration diagram of a biological fluid information acquisition device and biological information acquisition device according to a first embodiment of the present disclosure.

Hereinafter, the present disclosure will be schematically described first.

In order to solve the above-described problems, a biological fluid information acquisition device and biological information acquisition device according to a first aspect of the present disclosure includes: a light source configured to emit a laser beam; a light branching element configured to branch the laser beam into a first luminous flux and a second luminous flux; a first light receiving element configured to receive the first luminous flux; a second light receiving element configured to receive scattered light generated by scattering of the second luminous flux incident on an inspection site of a living body; a differential circuit to which the first light receiving element and the second light receiving element are coupled; a signal processing unit configured to obtain biological fluid information by processing a light detection signal output via the differential circuit; and a first light shielding part configured to reduce the scattered light incident on the first light receiving element.

According to the aspect, the first light shielding part configured to reduce the incidence of the scattered light on the first light receiving element is provided. As a result, mixing of the scattered light into the first light receiving element can be reduced, and the SN ratio of the light detection signal can be easily enhanced.

In a biological fluid information acquisition device and biological information acquisition device according to a second aspect of the present disclosure, in the first aspect, the light branching element is made of a light transmissive material, the first luminous flux is interface reflected light of the light branching element, and the second luminous flux is transmitted light that passes through the light branching element and is incident on the inspection site.

According to the aspect, the light branching element is made of a light transmissive material, the first luminous flux is the interface reflected light of the light branching element, and the second luminous flux is the transmitted light transmitted through the light branching element and incident on the inspection site. As a result, the light branching element that branches the laser beam into the first luminous flux and the second luminous flux can be achieved with a simple structure.

In a biological fluid information acquisition device and biological information acquisition device according to a third aspect of the present disclosure, in the second aspect, the light branching element is disposed at a position before emission of the laser beam to the inspection site of the living body.

In a biological information acquisition device according to a fourth aspect of the present disclosure, in the second aspect, the light branching element is disposed to be able to come into contact with the inspection site of the living body.

According to the third aspect or the fourth aspect, the light branching element that branches the laser beam into the first luminous flux and the second luminous flux can be achieved with a simple structure.

In a biological information acquisition device according to a fifth aspect of the present disclosure, in the fourth aspect, interface reflected light forming the first luminous flux is reflected light from a non-contact surface of the light branching element that does not come into contact with the inspection site.

In a biological information acquisition device according to a sixth aspect of the present disclosure, in the fourth aspect, a low reflection coat is provided on a contact surface of the light branching element that comes into contact with the inspection site.

According to the fifth aspect or the sixth aspect, because a main light ray of the reflected light from the contact surface of the light branching element that comes into contact with the inspection site is not incident on the first light receiving element, signal processing can be stably performed.

In a biological information acquisition device according to a seventh aspect of the present disclosure, in any one of the first to sixth aspects, a light amount adjustment mechanism is provided on an optical path to the first light receiving element, and the light amount adjustment mechanism adjusts an amount of light received by the first light receiving element to coincide with an amount of light received by the second light receiving element.

According to the aspect, because the light amount adjustment mechanism adjusts the amount of light received by the first light receiving element to coincide with the amount of light received by the second light receiving element, an SN ratio of the light detection signal can be easily enhanced.

In a biological information acquisition device according to an eighth aspect of the present disclosure, in the seventh aspect, the light branching element has a variable installation angle, and the light amount adjustment mechanism is capable of adjusting the amount of light received by the first light receiving element by changing the installation angle of the light branching element.

In a biological information acquisition device according to a ninth aspect of the present disclosure, in the seventh aspect, the light amount adjustment mechanism is a second light shielding part that is able to reduce the amount of light incident on the first light receiving element.

According to the eighth aspect or the ninth aspect, the light amount adjustment mechanism that adjusts the amount of light received by the first light receiving element can be easily achieved with a simple structure.

First Embodiment

Hereinafter, a biological information acquisition device according to a first embodiment of the present disclosure will be described in detail with reference to FIG. 1.

As illustrated in FIG. 1, the biological information acquisition device 100 includes a light source 3 that emits a laser beam 1, a light branching element 9 that branches the laser beam 1 into a first luminous flux 5 and a second luminous flux 7, a first light receiving element 11 that receives the first luminous flux 5, a second light receiving element 19 that receives scattered light 17 generated by scattering of the second luminous flux 7 incident on an inspection site 15 of a living body 13, a differential circuit 21 to which the first light receiving element 11 and the second light receiving element 19 are coupled, and a signal processing unit 27 that obtains biological fluid information 25 by processing a light detection signal 23 output via the differential circuit 21.

Further, a first light shielding part 29 that reduces incidence of the scattered light 17 on the first light receiving element 11 is provided.

In the embodiment, the biological information acquisition device 100 includes a case 2. The case 2 accommodates the light source 3, the light branching element 9, the first light receiving element 11, the second light receiving element 19, and the differential circuit 21. A hole 4 is open in a portion of the case 2 at which the second luminous flux 7 is incident on the inspection site 15 of the living body 13. In FIG. 1, the case 2 is illustrated with the portion of the hole 4 having a thickness, but the other portions are illustrated simply by a line diagram.

The first light shielding part 29 is a peripheral edge portion of the hole 4 of the case 2 and is configured by providing a light shielding member formed of a light transmissive material on an optical path through which the scattered light 17 is incident on the first light receiving element 11. A mark "X" in FIG. 1 represents a state in which the scattered light 17 is shielded by the first light shielding part 29. Examples of the light transmissive material include a carbon-based material, an ink-based material, a metal film, an alumite film having an anodized film thereof, and the like.

A collection lens 8 is disposed on the optical path of the scattered light 17 between the second light receiving element 19 and the hole 4 and is configured to collect faint scattered light scattered from a fluid, such as blood of a living body, and then to cause the collected scattered light to be incident on the second light receiving element 19. In FIG. 1, a reference numeral 26 indicates red blood cells.

The first light receiving element 11, the second light receiving element 19, and the differential circuit 21 are mounted on a circuit board 6. The circuit board 6 includes a portion of a light detection part 10 including the first light receiving element 11 and the second light receiving element 19, and a portion of a current-voltage conversion part 12 including the differential circuit 21.

The light detection part 10 outputs a current output by each of the first light receiving element 11 and the second light receiving element 19 as a detected current to the differential circuit 21 of the current-voltage conversion part 12.

The current-voltage conversion part 12 converts the detected current input from the light detection part 10 into a voltage signal and outputs the voltage signal as the light detection signal 23. Here, the differential circuit 21 converts the detected current input from the light detection part 10 into a voltage signal and outputs the voltage signal differentially. As a result, the SN ratio related to the light detection signal 23 output from the current-voltage conversion part 12 is enhanced.

The light detection signal 23 output from the current-voltage conversion part 12 is input to the signal processing unit 27. The signal processing unit 27 calculates and obtains biological fluid information 25 such as a blood flow, a blood volume, a blood flow rate, a pulse, and the like in biological tissue by processing the light detection signal 23.

As a method of obtaining the blood flow and the like in the biological tissue from the light detection signal 23, a known method can be applied, and thus description thereof will be omitted.

Light Branching Element

In the embodiment, the light branching element 9 is constituted of a plate member 14 made of a light transmissive material. The first luminous flux 5 is interface reflected light 31 of the light branching element 9, and the second luminous flux 7 is transmitted light 33 that passes through the light branching element 9 and is incident on the inspection site 15. Here, the interface reflected light 31 is configured so that reflected light 20 and 22 from interfaces of one surface 16 of a plate member 14 on the side of the light source 3 and the other surface 18 on the opposite side is incident on the first light receiving element 11.

Here, a material having a high transmittance with respect to the laser beam 1 can be used as the light transmissive material, and in the case of a visible light laser, glass, polycarbonate, acrylic, and the like are preferable.

In addition, in the embodiment, as illustrated in FIG. 1, the light branching element 9 is disposed at a position before emission of the laser beam 1 to the inspection site 15 of the living body 13.

Description of Actions of First Embodiment

Next, a procedure for acquiring the biological fluid information 25 of target body tissue by the biological information acquisition device 100 of the first embodiment will be described.

First, a portion of the hole 4 in the case 2 of the biological information acquisition device 100 of the embodiment is set on the inspection site 15 of the living body 13 and is fixed in that state. Then, the laser beam 1 is emitted from the light source 3. The laser beam 1 is branched into the first luminous flux 5 and the second luminous flux 7 by the light branching element 9. The first luminous flux 5 is received by the first light receiving element 11. The second luminous flux 7 is incident on the inspection site 15 of the living body 13 and is scattered, and the scattered light 17 is emitted to the outside from the hole 4 of the case 2. The emitted scattered light 17 is collected by the collection lens 8 and is received by the second light receiving element 19.

In this case, incidence of the scattered light 17 on the first light receiving element 11 is reduced by the first light shielding part 29.

Then, the light detection part 10 having the first light receiving element 11 and the second light receiving element 19, and the current-voltage conversion part 12 having the differential circuit 21 operate as described above and output the light detection signal 23. The light detection signal 23 is input to the signal processing unit 27 and calculated, and thus the target biological fluid information 25 is output.

Description of Effects of First Embodiment (1) According to the biological information acquisition device 100 of the embodiment, the first light shielding part 29 that reduces the incidence of the scattered light 17 on the first light receiving element 11 is provided. As a result, mixing of the scattered light 17 into the first light receiving element 11 can be reduced, and the SN ratio of the light detection signal 23 can be easily enhanced.

(2) In addition, in the embodiment, the light branching element 9 is made of a light transmissive material, the first luminous flux 5 is the interface reflected light 31 of the light branching element 9, and the second luminous flux 7 is the transmitted light 33 that is transmitted through the light branching element 9 and is incident on the inspection site 15. As a result, the light branching element 9 that branches the laser beam 1 into the first luminous flux 5 and the second luminous flux 7 can be achieved with a simple structure.

(3) In addition, in the embodiment, the light branching element 9 is disposed at a position before emission of the laser beam 1 to the inspection site 15 of the living body 13. As a result, the light branching element 9 that branches the laser beam 1 into the first luminous flux 5 and the second luminous flux 7 can be achieved with a simple structure.

Second Embodiment

Figure 2:
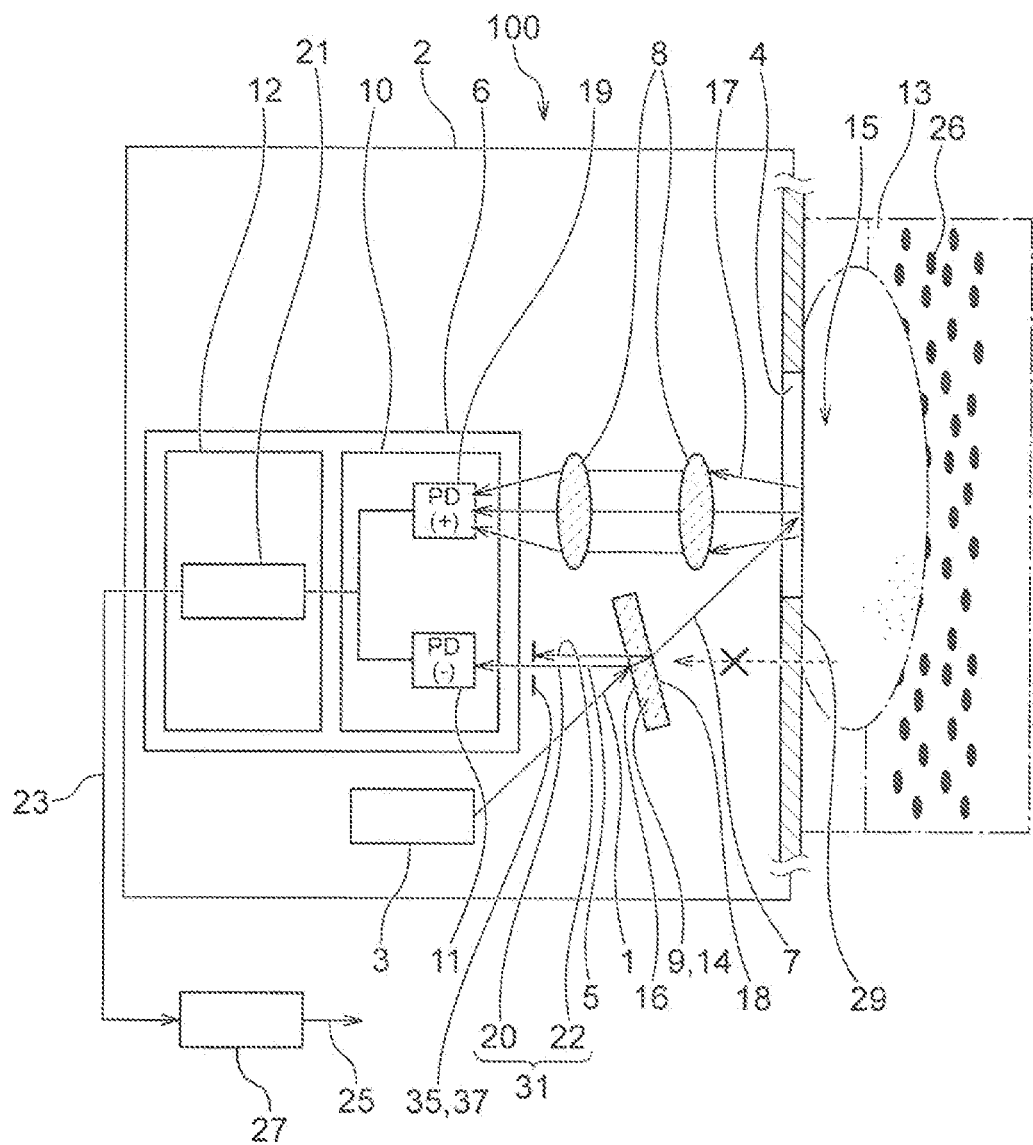
FIG. 2 is an overall schematic configuration diagram of a biological fluid information acquisition device and biological information acquisition device according to a second embodiment of the present disclosure.

Next, a biological information acquisition device 100 according to a second embodiment of the present disclosure will be described with reference to FIG. 2. Parts having the same configurations and effects as those in the first embodiment are designated by the same reference numerals, and description thereof will be omitted.

In the embodiment, a light amount adjustment mechanism 35 is provided on an optical path to the first light receiving element 11. Here, the light amount adjustment mechanism 35 is constituted of a second light shielding part 37 capable of reducing an amount of light of the first luminous flux 5 incident on the first light receiving element 11. Here, the second light-shielding portion 37 uses a pinhole having a variable area, but a variable dimming filter can also be used.

The light amount adjustment mechanism 35 is configured so that the amount of light received by the first light receiving element 11 is compared with the amount of light received by the second light receiving element 19 and is adjusted to coincide with the amount of light received by the second light receiving element 19 by a control part that is not illustrated.

Here, in the reflected light 20 and 22 forming the interface reflected light 31, the reflected light 22 is shielded by the second light shielding portion 37, and only the reflected light 20 is received by the first light receiving element 11.

According to the embodiment, because the light amount adjustment mechanism 35 adjusts the amount of light received by the first light receiving element 11 to coincide with the amount of light received by the second light receiving element 19, the SN ratio of the light detection signal 23 can be easily enhanced. Additionally, the light amount adjustment mechanism 35 that adjusts the amount of light received by the first light receiving element 11 can be easily achieved with a simple structure.

Third Embodiment

Figure 3:
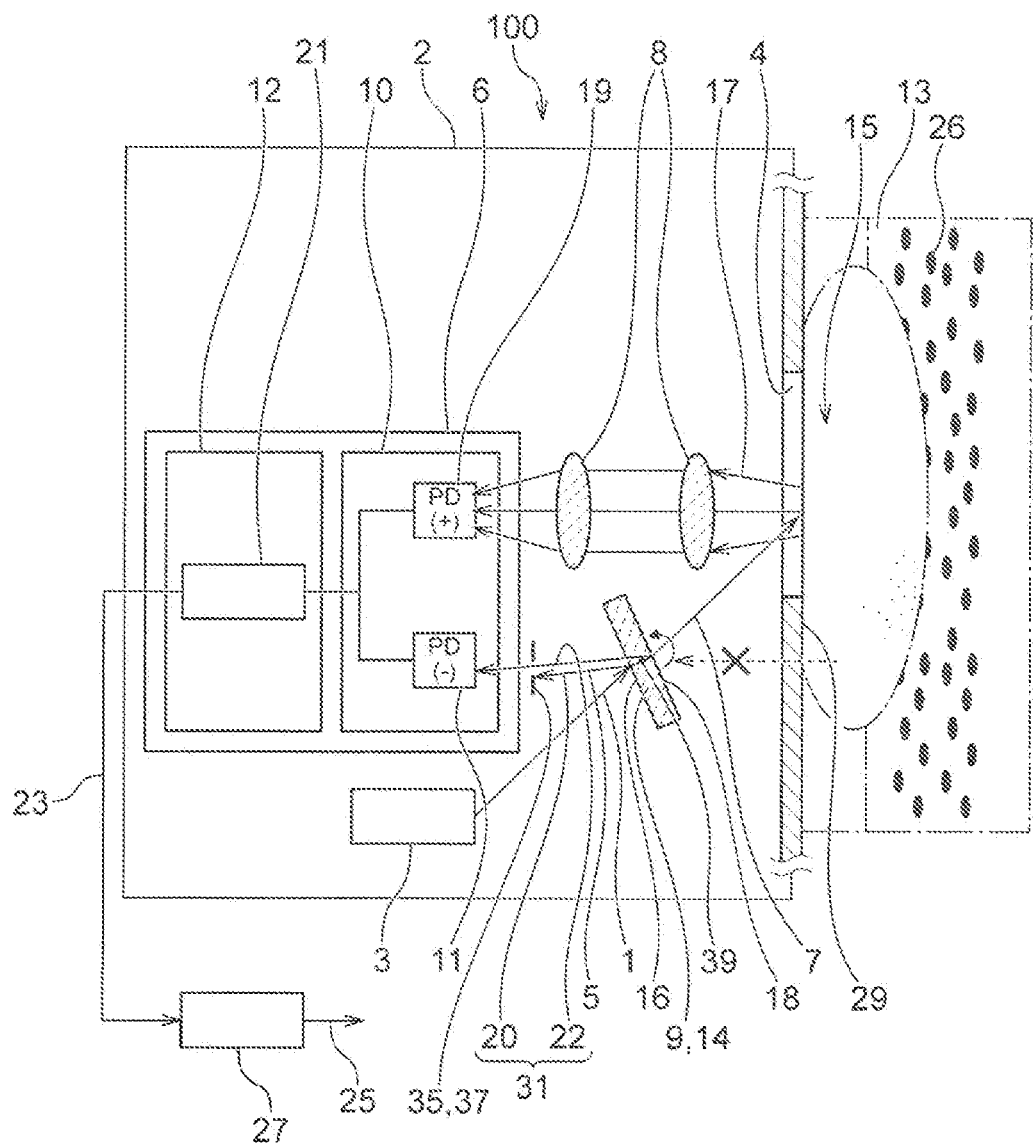
FIG. 3 is an overall schematic configuration diagram of a biological fluid information acquisition device and biological information acquisition device according to a third embodiment of the present disclosure.

Next, a biological information acquisition device 100 according to a third embodiment of the present disclosure will be described with reference to FIG. 3. Parts having the same configurations and effects as those in the first embodiment or the second embodiment are designated by the same reference numerals, and description thereof will be omitted.

In the embodiment, the light branching element 9 is configured to have a variable installation angle. Specifically, the light branching element 9 which is constituted of the plate member 14 with respect to a shaft 39 is configured to be rotatable by a drive mechanism which is not illustrated, and is configured to be able to fix a position thereof at an appropriate angle. An operation of the drive mechanism is also controlled by the control part which is not illustrated.

Additionally, the light amount adjustment mechanism 35 is configured to be able to adjust the amount of light received by the first light receiving element 11 by changing the installation angle of the light branching element 9. Here, in the reflected light 20 and 22 forming the interface reflected light 31, the reflected light 20 is shielded by the second light shielding part 37, and only the reflected light 22 is received by the first light receiving element 11.

According to the embodiment, the light level adjustment mechanism 35 that adjusts the amount of light received by the first light receiving element 11 can be easily achieved with a simple structure.

Fourth Embodiment

Figure 4:
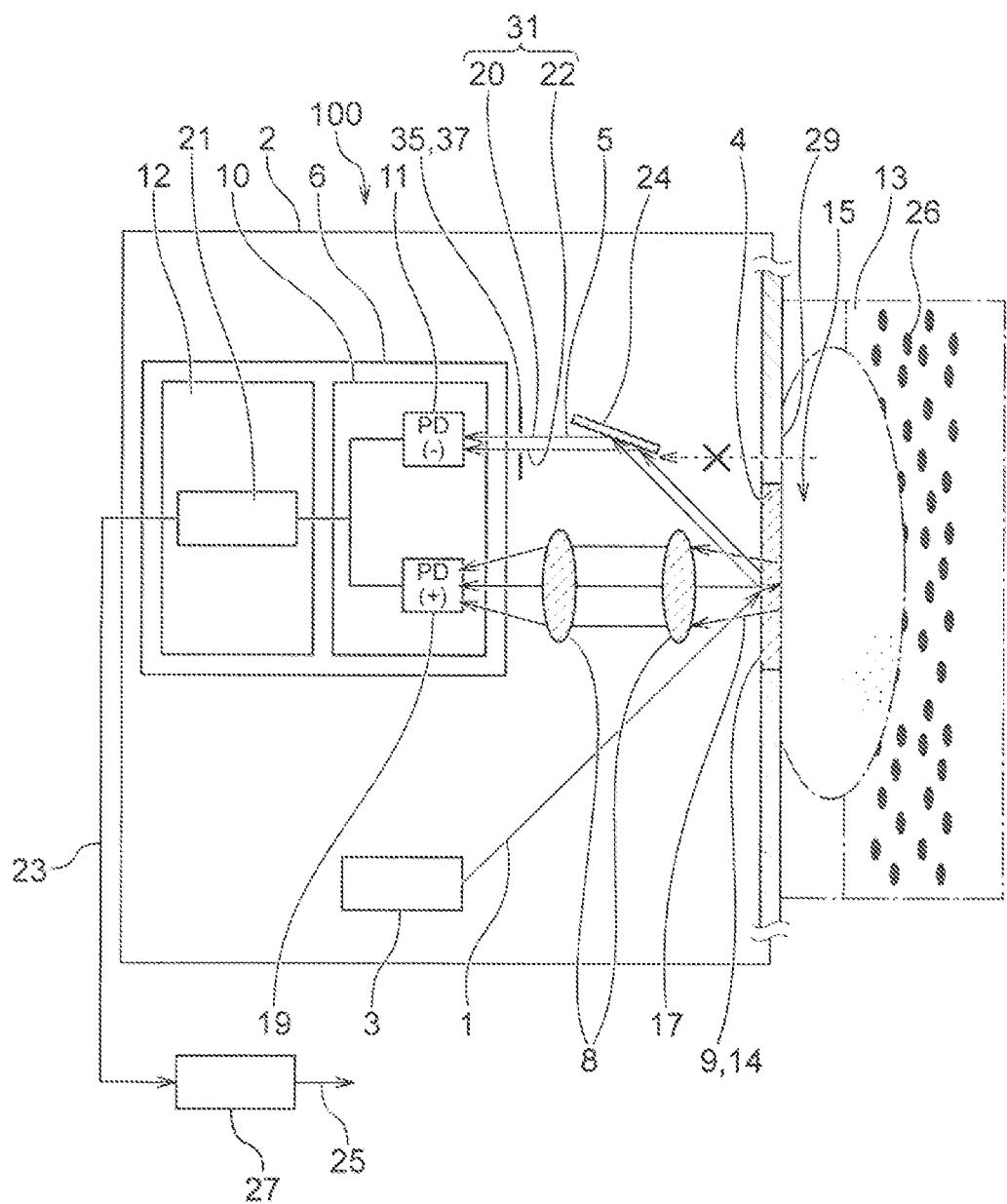
FIG. 4 is an overall schematic configuration diagram of a biological fluid information acquisition device and biological information acquisition device according to a fourth embodiment of the present disclosure.

Next, a biological information acquisition device 100 according to a fourth embodiment of the present disclosure will be described with reference to FIG. 4. Parts having the same configurations and effects as those in the first embodiment, the second embodiment, or the third embodiment are designated by the same reference numerals, and description thereof will be omitted.

In the embodiment, the light branching element 9 is constituted of the plate member 14 made of a light transmissive material and is disposed to be able to come into contact with the inspection site 15 of the living body 13. This point is different from the above embodiments. Specifically, as illustrated in FIG. 4, the light branching element 9 is installed in the hole 4 of the case 2. The interface reflected light 31 of the laser beam 1 forming the first luminous flux 5 from the light branching element 9 is received by the first light receiving element 11 via the reflection mirror 24. In the embodiment, the reflected light 20 and 22 forming the interface reflected light 31 is all received by the first light receiving element 11.

According to the embodiment, the light branching element 9 is disposed to be able to come into contact with the inspection site 15 of the living body 13. As a result, the light branching element 9 that branches the laser beam 1 into the first luminous flux 5 and the second luminous flux 7 can be achieved with a simple structure.

Fifth Embodiment

Figure 5:
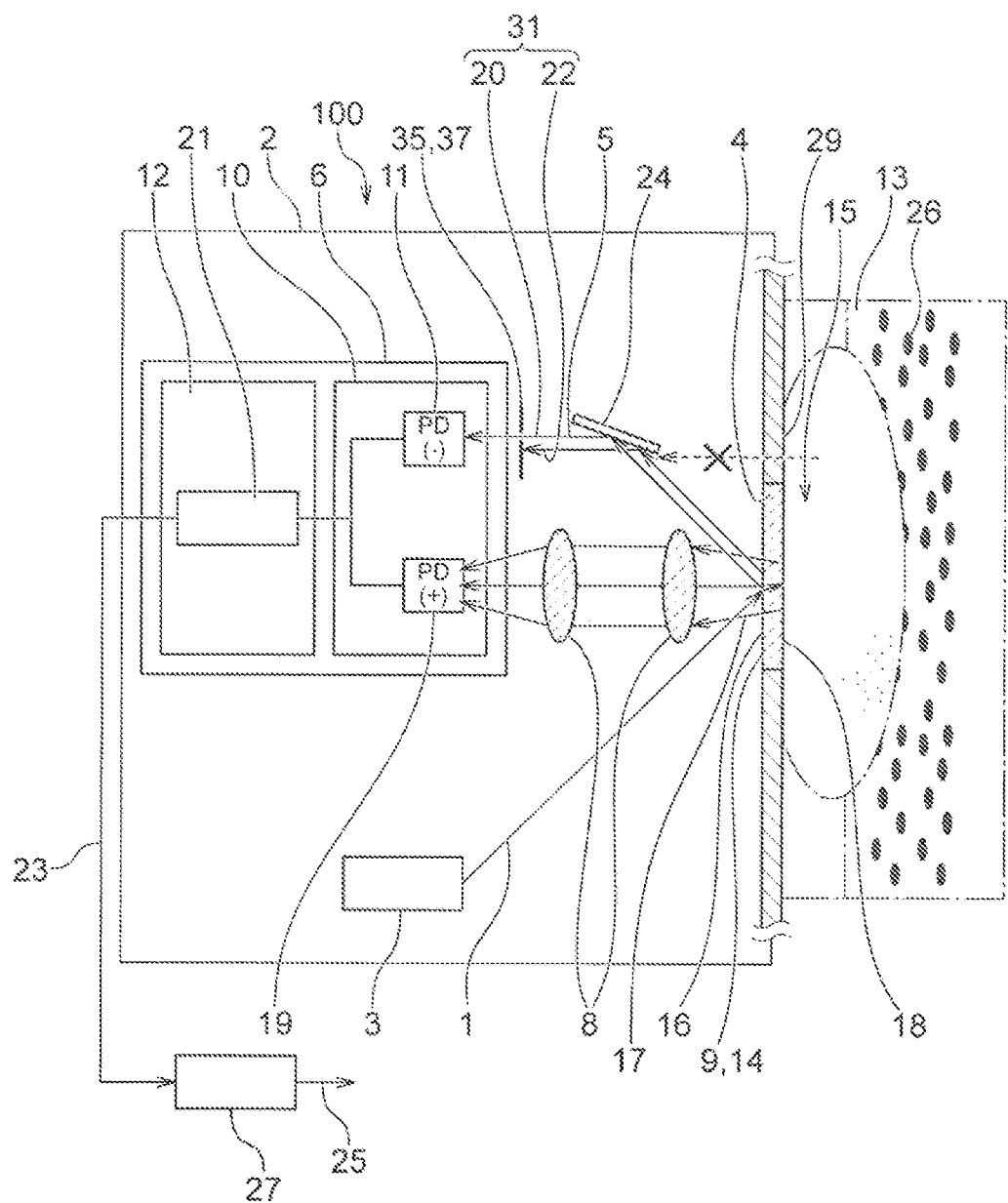
FIG. 5 is an overall schematic configuration diagram of a biological fluid information acquisition device and biological information acquisition device according to a fifth embodiment of the present disclosure.

Next, a biological information acquisition device 100 according to a fifth embodiment of the present disclosure will be described with reference to FIG. 5. Parts having the same configurations and effects as those in the first embodiment, the second embodiment, the third embodiment, or the fourth embodiment are designated by the same reference numerals, and description thereof will be omitted.

In the embodiment, unlike the fourth embodiment, the interface reflected light 31 forming the first luminous flux 5 is only the reflected light 20 from a non-contact surface of the light branching element 9 that does not contact the inspection site 15, that is, one surface 16 on the side of the light source 3. The reflected light 22 from the other surface 18 that comes into contact with the inspection site 15 is shielded by the second light shielding part 37.

According to the embodiment, because hardly any of the reflected light 22 from the other surface 18 of the light branching element 9 which is a contact surface that comes into contact with the inspection site 15 is incident on the first light receiving element 11, it is possible to stably carry out signal processing.

Sixth Embodiment

Figure 6:
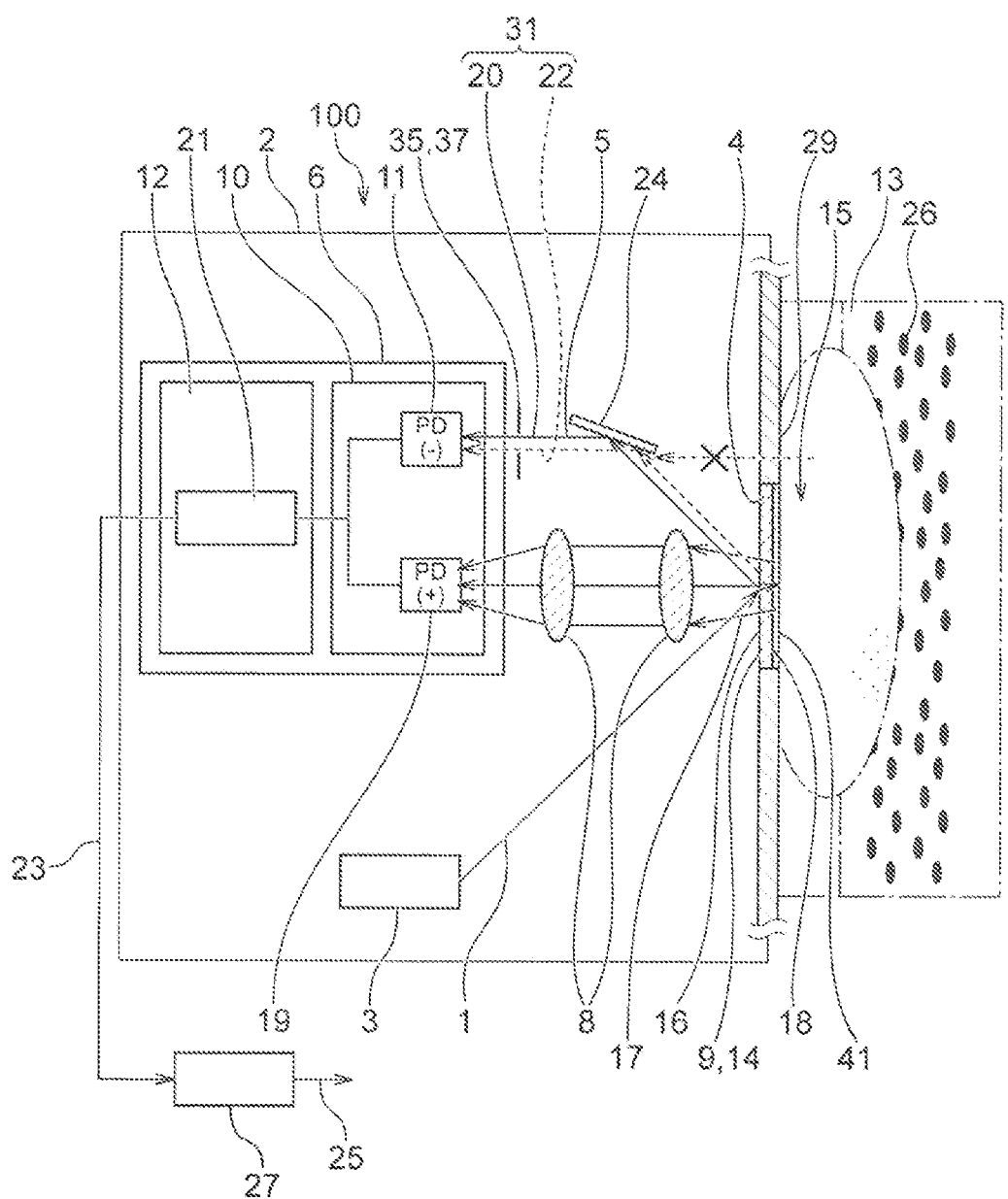
FIG. 6 is an overall schematic configuration diagram of a biological fluid information acquisition device and biological information acquisition device according to a sixth embodiment of the present disclosure.

Next, a biological information acquisition device 100 according to a sixth embodiment of the present disclosure will be described with reference to FIG. 6. Parts having the same configurations and effects as those in the first embodiment, the second embodiment, the third embodiment, the fourth embodiment, or the fifth embodiment are designated by the same reference numerals, and description thereof will be omitted.

In the embodiment, a low reflection coat 41 is provided on the other surface 18 of the light branching element 9 which is a contact surface that comes into contact with the inspection site 15. The low reflection coat 41 is made of a material capable of reducing the amount of reflected light 22 from the other surface 18 of the light branching element 9. In FIG. 6, a dashed line of the reflected light 22 indicates that the amount of light thereof is reduced by the low reflection coat 41. Here, specific materials of the low reflection coat 41 include silicon oxide, silicon nitride, magnesium fluoride, titanium oxide, zirconium oxide, and the like.

According to the embodiment, because hardly any of the reflected light 22 from the other surface 18 of the light branching element 9 which is the contact surface that comes into contact with the inspection site 15 is incident on the first light receiving element 11, it is possible to stably carry out signal processing.

Other Embodiments

Although the biological information acquisition devices 100 according to the embodiments of the present disclosure basically have the configurations described above, of course, it is possible to change or omit a partial configuration within a range that does not deviate from the gist of the present disclosure.

For example, the structure of the circuit board 6 is an example in the above description and may be any structure capable of obtaining the biological fluid information 25 from the light detection signal 23 output via the differential circuit 21.

What is claimed is:

1. A biological information acquisition device comprising:
   a light source configured to emit a laser beam;
   a light branching element configured to branch the laser beam into a first luminous flux and a second luminous flux, wherein
      the light branching element has a first surface, and a second surface opposite to the first surface,
      the first luminous flux is interface reflected light from the light branching element, and
      the interface reflected light includes
         first light reflected from the first surface, and
         second light reflected from the second surface;
   a first light receiving element configured to receive at least one of the first light reflected from the first surface or the second light reflected from the second surface;
   a second light receiving element configured to receive scattered light generated by scattering of the second luminous flux incident on an inspection site of a living body;
   a differential circuit to which the first light receiving element and the second light receiving element are coupled;

a signal processing unit configured to obtain biological fluid information by processing a light detection signal output via the differential circuit; and a first light shielding part configured to reduce the scattered light incident on the first light receiving element.

2. The biological information acquisition device according to claim 1, wherein the light branching element includes a light transmissive material, and the second luminous flux is transmitted light that passes through the light branching element and is incident on the inspection site.

3. The biological information acquisition device according to claim 2, wherein the light branching element is disposed at a position before emission of the laser beam to the inspection site of the living body.

4. The biological information acquisition device according to claim 2, wherein the light branching element is disposed so as to come into contact with the inspection site of the living body.

5. The biological information acquisition device according to claim 4, wherein the first surface does not come into contact with the inspection site.

6. The biological information acquisition device according to claim 4, wherein a low reflection coat is provided at the second surface that comes into contact with the inspection site.

7. The biological information acquisition device according to claim 1, wherein a light amount adjustment mechanism is provided on an optical path to the first light receiving element, and the light amount adjustment mechanism is configured to adjust an amount of one of the first light or the second light received by the first light receiving element to coincide with an amount of the scattered light received by the second light receiving element.

8. The biological information acquisition device according to claim 7, wherein the light branching element has a variable installation angle, and the light amount adjustment mechanism is further configured to adjust the amount of the one of the first light or the second light received by the first light receiving element by changing the variable installation angle of the light branching element.

9. The biological information acquisition device according to claim 7, wherein the light amount adjustment mechanism is a second light shielding part that is configured to reduce the amount of the one of the first light or the second light incident on the first light receiving element.

* * * * *